United States Patent [19]

Vesely et al.

[11] 4,259,317

[45] Mar. 31, 1981

[54] PREPARATION FOR THE PROTECTION OF EMERGING SUGAR BEETS AGAINST DAMPING-OFF, AND METHOD OF ITS PRODUCTION

[75] Inventors: Dáša Vesely, Prague; Slavomil Hejdánek, Roxtoky u Prahy, both of Czechoslovakia

[73] Assignee: Vyzkummy ustav rostlinné výroby, Prague, Czechoslovakia

[21] Appl. No.: 54,793

[22] Filed: Jul. 5, 1979

[30] Foreign Application Priority Data

Jul. 5, 1978 [CS] Czechoslovakia .................. 4462-78

[51] Int. Cl.³ ............................................. A01N 63/00
[52] U.S. Cl. ...................................... 424/93; 47/57.6; 71/77
[58] Field of Search ................ 424/93; 47/57.6; 71/77

[56] References Cited

U.S. PATENT DOCUMENTS

| | | | |
|---|---|---|---|
| 1,319,157 | 10/1919 | Lingle | 47/57.6 |
| 2,502,809 | 4/1950 | Vogelsang | 47/57.6 |
| 2,651,883 | 9/1953 | Hedrick et al. | 47/57.6 |
| 2,764,843 | 10/1956 | Peake | 47/57.6 |
| 2,967,376 | 1/1961 | Scott | 47/57.6 |
| 3,936,976 | 2/1976 | Porter et al. | 47/57.6 |
| 4,061,488 | 12/1977 | Mann | 47/57.6 |
| 4,067,141 | 1/1978 | Matsunaga et al. | 47/57.6 |
| 4,068,602 | 1/1978 | Mickus et al. | 47/57.6 |

FOREIGN PATENT DOCUMENTS

| | | | |
|---|---|---|---|
| 2317881 | 11/1977 | France | 424/93 |
| 800736 | 9/1958 | United Kingdom | 424/93 |
| 972871 | 10/1974 | United Kingdom | 424/93 |
| 246958 | 11/1969 | U.S.S.R. | 424/93 |
| 302914 | 1/1979 | U.S.S.R. | 424/93 |

*Primary Examiner*—Shep K. Rose

[57] ABSTRACT

The invention relates to a dry powdered preparation to be applied onto sugar beet seeds, the preparation containing, as its active constituent, organs of reproduction of *Pythium oligandrum* Drechsler, particularly the oospores, in a sufficiently high concentration of at least about 1,000,000, preferably at least about 4,000,000 per gram (optimum in the range 50,000,000–500,000,000 per gram). Such concentrations make it possible to apply about 100,000 oospores or more onto every seed, which proved sufficient to secure protection of emerging sugar beet plants against "damping off" or "black leg" disease. Although the mycoparasitism of *Pythium oligandrum* has been discovered many years ago, its use for biological protection required a lot of research work establishing the conditions necessary for obtaining reliable results on a field scale.

4 Claims, No Drawings

PREPARATION FOR THE PROTECTION OF EMERGING SUGAR BEETS AGAINST DAMPING-OFF, AND METHOD OF ITS PRODUCTION

BACKGROUND OF THE INVENTION

It is known that emerging sugar beet plants are often affected by parasitic fungi present in the soil, such as *Pythium ultimum, Pythium debaryanum*, various species of the Aphanomyces and Fusarium genus, as well as by *Rhizoctonia solani* and others. *Pythium oligandrum* had been considered a mild parasite too. Said parasites are the cause of the known disease called usually "damping off" or "black leg", capable of destroying a great deal of emerging sugar beet plants, particularly in a cold weather. The disease attacks mainly the sprouting up seeds, mostly prior to the sprout penetrating the soil surface. The disease usually dies away as soon as the first pair of true leaves is formed. Thereby it is possible to explain the fact that the damages caused by the damping off were not too serious in the past when natural seed clusters were seeded in an amount of 25 to 30 kg per hektar. Then about 1,500,000 of plants per hektar emerged and superfluous seedlings were removed simultaneously with weak or apparently diseased plants at a stage when true leaves were already grown and the disease passed away. The method was, however, uneconomical, demanding a great deal of manual labor. Nowadays considerably lower doses of ground-off or genetically one-bud seeds are used so that only about 200,000 plants per hektar emerge and no superfluous plants need to be removed. The method is, as such, very economical, the damping-off, however, appears to be much more damaging than in the past, often decreasing the crops quite seriously. Therefore, the damping-off of emerging sugar beet becomes the limiting factor barring a more extensive use of modern cultivating methods, at which the sugar beet is seeded in definitive distances and requires no manual labor. The only way to protect emerging sugar beet plants against "damping off" was, until now, soaking or dressing of the seed with fungicides containing mostly organic derivatives of mercury and sulfur.

Said fungicides are effective but simultaneously noxious for animals and for human health, and it can be expected that their use will be successively reduced to protect the biosphere from a pollution.

Mercury accumulates in the soil and penetrates into plants, herbivorous animals and fish in water-courses and gets, through the nutrition chain, into human body where it causes long lasting degenerative damages. Sulfur compounds, though often considered comparatively harmless, are nevertheless toxic enough. So e.g. tetramethylthiuram disulphide (TMTD) has a rather low $LD_{50}$–865 mg per kg of live weight. The dust of pulverulent TMTD, being about 5 times more toxic than some systemic fungicides, endangers particularly the labor at seed dressers and seeding machines, affecting seriously human nervous system. There are known no effective and simultaneously fully harmless fungicides capable of protecting sugar beet against the "black leg" disease.

Said disease is caused mainly by micromycetes of the Pythium genus, particularly by *Pythium ultimum* and *P. debaryanum*.

*Pythium oligandrum* was discovered in 1930 on the pea roots as one of pathogenic agents. The discoverer, C. Drechsler, has found, when studying fungi causing rot of roots and other parts of products and fruits of various cultivated plants such as tomatoes and watermelons in the South of the U.S.A. already in 1943 that *Pythium oligandrum* parasites on various other pathogenic species of the same genus such as on *Pythium ultimum* and *Pythium debaryanum* (Drechsler, C., Phytopathology 33, 1943, 4, 261–299). More recently J. W. Deacon studied analogical biotic relations of *Pythium oligandrum* to microorganisms parasiting on grain (e.g. *Gaeumannomyces graminis*) and mentioned also that he succeeded in controlling a wheat disease caused by *Pythium ultimum* by inoculating the soil simultaneously with *Pythium oligandrum* and *Pythium ultimum* (Trans. Br. Soc. 66 /3/, 383–391). Said author offered his opinion that the result might be caused by nutrition competition or, perhaps, also by direct weakening of the parasitic *Pythium ultimum* by the mycoparasitic *Pythium oligandrum*. The existence of mycoparasitism in the rhisosphere of sugar beet was neither proved nor disclosed as yet.

The endeavour to check the damping-off was directed rather to the breeding of resistant sugar beet strains, compare e.g. F. Koch (Gruppo gior. edagric. 20, 1974, 1–2, 8–12), which author included, in agreement with others, *Pythium oligandrum* into the same group of pathogens as e.g. *Pythium ultimum* and *Pythium irregulare*. Another repeatedly tried way to control said disease was the utilization of the antibiosis. There were produced and tested several preparations based on the production of antiobiotics by certain micromycetes such as *Trichoderma viride*. There are, however, serious objections from the medical point of view against the use of antibiotics in agriculture especially that in repeated contact of agricultural workers with antibiotics in lower-effective doses, resistant strains of pathogenic microorganisms can be developed. Moreover, the suggested antibiotics possess but a narrow spectrum of activity and their effect in the practice is rather uncertain, depending on the weather and soil condition, e.g. on the humidity and on the contingent presence of antagonists in the soil. Inoculated microorganisms capable of producing antibiotics succumb not only to antagonists but also to parasites and are even liable to stimulate the growth of some pathogens.

GENERAL DISCLOSURE

The inventors studied systematically the flora of the rhizosphere of sugar beet and tried, with some success, to protect the emerging plants by applying the oospores of *Pythium oligandrum* Drechsler onto the seeds in the form of an aqueous suspension, compare e.g. D. Veselý, Use of *Pythium oligandrum* Drechsler in Protection of emerging sugar beet, Abstract of Papers, 3rd International Congress of Plant Pathology, 16–23 Aug., 1978, Munic, or D. Veselý, Biological Protection of emerging sugar beet against damping-off established by mycoparasitism in non-sterilized soil, Zbl. Bakt. II. Abt., Bd. 133, 436–443, and other papers of the same author. The inventors also developed a submerse cultivation method of *Pythium oligandrum* to obtain suspensions of oospores to be applied onto the sugar beet seed. Recently, the inventors found, however, that it is difficult to obtain the necessary concentration of vigorous oospores when using aqueous suspensions.

The invention is based on more detailed studies proving that *Pythium oligandrum* is more widely spread in soils than expected until now and that it is controlled by various antagonists and hyperparasites so that it cannot be often discovered unless a more systematic research is carried out at different localities and in different time intervals. The inventors established the fact that it is necessary to apply the *Pythium oligandrum* oospores in unusually high quantities onto the seed to secure reliable protection, avoiding a premature destruction of the mycoparasite, preferably more than 100,000 oospores per seed in average, and that this cannot be reliably achieved if using aqueous suspensions of the oospores.

Moreover, liquid aqueous preparations are too unstable, keeping their activity not more than for two weeks. Therefore, during usual storage and distribution a considerable portion of the oospores looses its sprouting ability or, at least, its vigor due to the autolysis or contamination with hyperparasites.

It has been found now that above mentioned inconveniences can be removed by a new pulverulent preparation which contains at least one million, (optimum 50,000,000–500,000,000) of live and vigorous oospores and other propagation organs per gram. The finely powdered preparation adheres well to the seed surface even in absence of adhesives. If desired, a comparatively small amount of suitable dried adhesives may be added to ensure a suitably thick dressing. The preparation consists of dried and ground fermented farinaceous substrate, preferably solid grain or corn substrate on which *Pythium oligandrum* was bred in a stationary manner under conditions favoring the sporulation, particularly in presence of 2–3 percent of caucium chloride in the added liquid nutrient and while irradiating the fermenting substrate with visible, preferably blue or green light.

Prior to using such high concentrations of the mycoparasite spores it had to be established whether the natural equilibrium between various soil microorganisms would not be permenently and undesirably affected. Fortunately it has been found that the original equilibrium is rapidly renewed by various microorganisms destroying the excess of *Pythium oligandrum* and that the protection lasts only for a rather short period of time necessary to shield the seedlings from the parasites during the critical period of the growth. Thus, the biological protection of sugar beet by means of the preparation according to the invention does not introduce any foreign microorganism into the soil—*Pythium oligandrum* belonging to the habitual microflora—and change the natural equilibrium of it but temporarily and locally, just in the narrow surroundings of the sugar beet roots. Among microorganisms controlling *Pythium oligandrum* there can be mentioned several species of the genus Drechslera and Mucor, all ubiquitous in the cultivated soil, and in the rhisosphere of sugar beet plants.

Other propagation organs than oospores are gemmae and oogonia, usually present in minor amounts.

Surprisingly, in spite of the alleged facultative parasitism of *Pythium oligandrum* the preparation of the invention stimulates the growth of sugar beet plants which are in average visibly more vigorous and healthy than the controls treated either with TMTD or with other usual pesticides, or not treated at all.

To increase the number of propagation organs on the seed, it is possible to apply, the pulverous preparation onto a slightly wet seed. Thereby a thicker layer of the preparation on the seed is formed. Addition of dry adhesives to the dry preparation is also feasible though usually superflueus, the ground mycellium and substrate adhering very good to the seed surface, especially if the latter had been slightly wetted just prior to the application of the preparation, and preferably just prior to seeding as well. The seed can be slightly wetted instead of water with aqueous solutions of substances stimulating the growth and simultaneously increasing the adhesion of the powdered preparation, e.g. with diluted solutions or suspensions of organic and inorganic fertilizers or thickening agents. The effect on the thickness of the dressing layer is similar like that of the known dressing processes. The usual dressing with addition of the powdered preparation of the invention is also feasible, provided that the propagation organs of *Pythium oligandrum*, present therein, are not damaged by any constituent of the dressing which should be sterile but for the oospores of *Pythium oligandrum*.

The preparation is produced preferably by covering aluminium or plastic plates with an about 1–2 cm thick layer of sterilized grains such as husked millet. Said layer is then soaked with a suitable liquid nutrient and the substrate thus obtained is sterilized in a steam autoclave at 120° C. for 30 minutes. Inoculation of the substrate is carried out by sprinkling or spreading homogeneously an aqueous suspension of oospores of *Pythium oligandrum*, using about 200 ml of the suspension per kg of the grains. For the suspension of oospores sterilized distilled water can be used. The inoculated substrate is cultivated for 14 days at 25° C. in a special climatized semi-sterile cultivation room. During the cultivation the growth of *Pythium oligandrum* is checked microscopically about the degree of fructification and about the growth condition and the eventual contamination as well. After the finished cultivation the vitality and the fructification degree of the mycellium is checked biologically. The end of the cultivation depends substantially on the reached optimum production of oospores which should exceed one million, optimum in the range 50,000,000–500,000,000 of oospores per gram of dried fermented substrate.

The above described method proved to be best for reaching high fructification, particularly if the fermenting substrate is irradiated with blue or green light. Its another advantage is, in comparison with wet aerated submerse cultivation, better economy, the amount of water to be evaporated being very low. The drying of the mycoparasite together with the fermentation substrate can be carried out in any suitable way using e.g. a band drier at temperatures not exceeding 35° C., preferably not exceeding 30° C. Another suitable drying method is lyophilization. The dried material is then ground and homogenized, maintaining the above said temperature limit. The powdered material should be very fine so that it adhered easily to the rough seed surface. Biological check-up establishes the vitality and number of oospores. At exceedingly high amounts of oospores the concentration can be adjusted by adding inert powdered material, usually however the homogenization by mixing several batches is quite satisfactory since the surplus of oospores is better than scantiness. Regarding the above explained relations between parasites, mycoparasites and hyperparasites in the rhizosphere a surplus of oospores of *Pythium oligandrum* cannot cause any harm. On the other hand, it secures practically complete elimination of diseases caused by fungi. High numbers of oospores on the seed surface, preferably not less than 100,000 per one seed, protects the sprouting seed from parasiting fungi not only be direct elimination thereof due to the mycoparasitism, but also by making competitive relations impossible by sheer overwhelming quantity. The combination of said two factors is apparently decisive for obtaining satisfactory results in practice, no chance being given either to antagonists or to parasites of any kind to destroy completely *Pythium oligandrum* during the time interval necessary for effective protection.

The sporulation can be supported by irradiating stationary cultures with visible light, preferably using blue or green filters (440–550 nm).

Crucial conditions found by the inventors are:
(a) dry powdered preparation, and
(b) an unusually high concentration of oospores, namely at least about 1,000,000, (optimum in the range 50,000,000–500,000,000 per gram) measured in a known way using a Bürker's chamber.

The most suitable method for producing such powdered preparation consists in cultivating *Pythium oligandrum* in stationary cultures on grain or corn substrate wetted with liquid nutrients containing, in addition to usual constituents such as sugars, corn-steep liquor, and mineral salts, from 2 to 3 percent of calcium chloride. The sterilized substrate is then inoculated with *Pythium oligandrum* Drechsler and the cultivation is carried out preferably at semisterile conditions, the substrate being irradiated by visible light, advantageously through a blue or green filter.

Another feasible method consists in submerse cultivation of *P. oligandrum* and subsequent dehydration of the fermented mash either by adding substances capable of binding water such as sugars, starch or mineral salts, or by lyophilization, or by spray-drying. In any case, the substance is dried and ground at temperatures not exceeding 35° C. The powdered preparation thus obtained is ready for use and can be stored for several months without loosing most of its activity.

EXAMPLE 1

Millet grain sterilized at 120° C. was spread in a 1.5 cm thick layer on aluminium plates, soaked with liquid nutrient consisting of an aqueous solution containing 3% of sacharose, 3% thickened corn-steep liquor, and 2.5% of calcium chloride, with pH 5.5 to 6.0, and inoculated with an inoculum of *Pythium oligandrum*, prepared in following way:

Vegetative inoculum out of selected and tested culture was propagated in a nutrient consisting of
Potato starch: 30 g
Ammonium sulfate: 15 g
Potassium dihydrogen phosphate: 5 g
Magnesium sulfate: 0.5 g
Dried yeast: 10 g
Calcium carbonate: 10 g
Soya bean flower: 50 g
Water: 1000 g
(pH 6.0, sterilized at 120° C. for 30 minutes).

The cultivation was carried out in a reciprocating shaker, amplitude 10.5 cm, 96 swings per minute, 20° C., 48 hours.

The culture was used as inoculum for sterilized millet grains, soaked previously with following boiling solution:
Zinc sulfate: 50 p (weight)
Potassium dihydrogen phosphate: 150 p
Manganese sulfate: 50 p
Calcium chloride: 250 p
Water: 200,000 p The grain should not be sticky; single grains are discrete.

The substrate was distributed into 500 ml Erlenmayer flasks, 50 ml into each (25–30). After having been sterilized two times at 120° C. for 40 min., in a time interval of 24 hours, under a cotton-wool stopper covered with calico, each flask was inoculated with 3–4 ml of the above described inoculum. The cultivation was carried out in a thermostat at 18°–20° C., at a relative air humidity 80–90%, for 10–14 days. Thereafter the content was tested for sterility and the number of oospores per gram of millet grain was checked using a Bürker chamber. The preserves are stored at −10° C. and used as inoculum for the substrate on the aluminium plates, prepared as described above.

The cultivation was carried out at semi-sterile condition, in a climatized room at 25° C. for 14 days, in the light of 500 W bulb covered with a blue filter (435–480 nm).

After biological checking of vitality of spores and miscroscopic checking of the sporulation degree the fermented substrate was dried on a band drier at 30°–35° C. and the dried mass was carefully ground so as not to exceed the same temperature. Several batches were homogenized together and the product was packed and stored. It contained about 25,000,000 of oospores per gram.

The activity was not decreased substantially after 2–3 month storage in cool, dry and dark space.

The preparation adhered easily onto sugar beet seeds, the number of oospores on every seed being at least 100,000. The protection was at least equal to that achieved with effective chemical preparations. The powder can be applied onto sugar beet seed and the seed stored for several months without loosing the protective effectivness.

EXAMPLE 2

The cultivation was carried out in the way disclosed in Example 1, the liquid sporulation nutrient possessing, however, following composition: 3% of thickened corn-steep liquor, 3% of sacharose, 2.5% of calcium chloride, 0.5% of zinc sulfate and 0.2% of manganese sulfate. The number of oospores in dried product was about 40,000,000 per gram.

Although the invention is described with reference to a plurality of preferred embodiments thereof, it is to be expressly understood that it is in no way limited to the disclosure of such a plurality of preferred embodiments, but is capable of numerous modifications within the scope of the appended claims.

What is claimed is:

1. A preparation for the protection of emerging sugar beets against damping-off and for simultaneously stimulating the growth of seedlings when applied in the amount of at least 100,000 oospores on each of the seeds, such preparation comprising a dried and powdered grain substrate fermented with *Pythium oligandrum* Drechsler and containing at least about 1,000,000 oospores per gram.

2. A preparation according to claim 1, wherein the preparation contains from about 50,000,000 to 500,000,000 oospores per gram.

3. A method of manufacturing a preparation for the protection of emerging sugar beet plants against damping-off, and also for stimulating the growth of seedlings when applied on seeds, said method comprising wetting grain material with a liquid nutrient, fermenting the wetted material with *Pythium oligandrum* Drechsler, drying the fermented material and grinding it at temperatures not exceeding 35° C., the fermented material containing at least 1,000,000 oospores of *Pythium oligandrum* Drechsler per gram of dry substance.

4. A method according to claim 3, wherein the wetted material is spread on flat plates, and is irradiated during the fermentation by visible light, using blue or green filters.

* * * * *